(12) United States Patent
Hausmanns et al.

(10) Patent No.: US 12,138,297 B2
(45) Date of Patent: Nov. 12, 2024

(54) COLLAGEN HYDROLYSATE FOR USE WITH SKIN DISORDERS AND INTESTINAL DISORDERS

(71) Applicant: GELITA AG, Eberbach (DE)

(72) Inventors: Stephan Hausmanns, Heidelberg (DE); Steffen Oesser, Glücksburg (DE); Franziska Dolle, Eberbach (DE); Hans-Ulrich Frech, Weinheim (DE)

(73) Assignee: GELITA AG, Eberbach (DE)

( * ) Notice: Subject to any disclaimer, the term of this patent is extended or adjusted under 35 U.S.C. 154(b) by 572 days.

(21) Appl. No.: 17/350,280

(22) Filed: Jun. 17, 2021

(65) Prior Publication Data

US 2021/0308231 A1  Oct. 7, 2021

Related U.S. Application Data

(63) Continuation of application No. PCT/EP2019/086839, filed on Dec. 20, 2019.

(30) Foreign Application Priority Data

Dec. 21, 2018 (DE) .................... 10 2018 133 374.9

(51) Int. Cl.
| | | |
|---|---|---|
| *A61P 17/04* | (2006.01) | |
| *A61K 9/00* | (2006.01) | |
| *A61K 31/573* | (2006.01) | |
| *A61K 38/01* | (2006.01) | |
| *A61K 38/39* | (2006.01) | |
| *A61P 17/00* | (2006.01) | |

(52) U.S. Cl.
CPC ............ *A61K 38/39* (2013.01); *A61K 9/0014* (2013.01); *A61K 9/0053* (2013.01); *A61K 31/573* (2013.01); *A61K 38/014* (2013.01); *A61P 17/00* (2018.01); *A61P 17/04* (2018.01)

(58) Field of Classification Search
None
See application file for complete search history.

(56) References Cited

U.S. PATENT DOCUMENTS

| | | | | |
|---|---|---|---|---|
| 9,072,724 | B2 * | 7/2015 | Hausmanns | A61K 8/65 |
| 11,673,940 | B2 * | 6/2023 | Hausmanns | A61Q 3/00 |
| | | | | 514/18.8 |
| 2013/0252899 | A1 * | 9/2013 | Hausmanns | A61K 38/39 |
| | | | | 530/356 |
| 2014/0255485 | A1 * | 9/2014 | Frech | A61P 17/02 |
| | | | | 424/94.4 |

FOREIGN PATENT DOCUMENTS

| | | | |
|---|---|---|---|
| CN | 104382943 | A | 3/2015 |
| DE | 100 58 772 | A1 | 6/2002 |
| DE | 698 25 495 | T2 | 7/2005 |
| DE | 102010060564 | A1 | 5/2012 |
| DE | 102012101911 | A1 | 9/2013 |
| EP | 1 140 021 | B1 | 8/2004 |
| RO | 115690 | B1 | 5/2000 |
| RO | 115691 | B * | 5/2000 |
| WO | WO 2012/065782 | A2 | 5/2012 |
| WO | WO-2019224035 | A1 * | 11/2019 ........... A61K 31/573 |

OTHER PUBLICATIONS

Monk et al. ("Anthralin-corticosteroid combination therapy in the treatment of chronic plaque psoriasis," Arch Dermatol. Apr. 1988; 124(4):548-50) (Year: 1988).*
Walling et al. ("Update on the management of chronic eczema: new approaches and emerging treatment options," Clin Cosmet Investig Dermatol. 2010; 3: 99-117) (Year: 2010).*
International Search Report in International Application No. PCT/EP2019/086839, mailed on Jun. 23, 2020.
Oikarinen et al., "A New Method to Measure Type I and III Collagen Synthesis in Human Skin In Vivo: Demonstration of Decreased Collagen Synthesis After Topical Glucocorticoid Treatment," *Journal of Investigative Dermatology*, vol. 98, Issue 2 (1992) pp. 220-225.
Thompson Scientific, London, GB; vol. 2015, No. 31, AN 2015-25050D, Retrieved from: Database WPI [online], XP002798648.

* cited by examiner

*Primary Examiner* — Christina Bradley
(74) *Attorney, Agent, or Firm* — Leydig, Voit & Mayer, Ltd.

(57) ABSTRACT

The present invention relates to collagen hydrolysate for use as an active substance in the treatment of inflammatory skin disorders and intestinal disorders and/or skin disorders and intestinal disorders accompanied by inflammation.

15 Claims, 5 Drawing Sheets

COLLAGEN HYDROLYSATE FOR USE WITH SKIN DISORDERS AND INTESTINAL DISORDERS

CROSS-REFERENCE TO RELATED APPLICATIONS

This patent application is a continuation of co-pending International Patent Application No. PCT/EP2019/086839, filed Dec. 20, 2019, which claims the benefit of German Patent Application No. 10 2018 133 374.9, filed Dec. 21, 2018, each of which is incorporated by reference in its entirety herein.

FIELD OF THE INVENTION

The present invention relates to collagen hydrolysate for use as an active substance in the treatment of inflammatory skin disorders and intestinal disorders and/or skin disorders and intestinal disorders accompanied by inflammation.

The invention also relates to collagen hydrolysate for use as an active substance to alleviate side effects of corticosteroids, in particular their side effects on the skin.

BACKGROUND OF THE INVENTION

Neurodermatitis, which is also referred to as atopic eczema, is a chronic skin disorder which, in industrialised countries, currently affects 1 to 3% of adults and 5 to 20% of children. The incidence of neurodermatitis is generally increasing, and since the middle of the 20th century there has been a fourfold to sixfold increase in the occurrence of the disorder. Although the exact cause of the disorder is not yet fully understood, according to the current state of research it is an autoimmune disorder in which both a genetic predisposition and environmental influences play a role.

Neurodermatitis generally manifests itself in the form of an impaired skin barrier function, with specific symptoms being, in particular, reddened, scaly, sometimes also weeping eczema. These are associated with acute or chronic itching, which may be very intense and often continues through the night as well. In particular, the itching may significantly impair the quality of life of the individuals affected. The severity of the neurodermatitis can be assessed in accordance with the SCORAD (Scoring Atopic Dermatitis) index.

Until now, it has not been possible to completely cure neurodermatitis, however, various approaches are available for treating the symptoms. The main focus here is on basic skin care in the form of a topical treatment with ointments, creams or lotions in order to stabilize the barrier function and reduce the sensitivity of the skin to irritation and the infiltration of allergens. Should this measure no longer be sufficient in the case of a more severe manifestation of the disorder or the symptoms, corticosteroids in particular are used as a therapeutic measure as anti-inflammatory agents. These preparations with cortisol effect are often referred to in everyday language as cortisone. They are usually applied topically to the affected skin areas, although they are only suitable for short-term application due to the known side effects of corticosteroids, in particular even on the skin (for example skin atrophy, pigment disorders and ecchymosis).

There is thus a great need for active substances for the treatment of neurodermatitis and other disorders which are accompanied by fewer side effects and which can be used alternatively or additionally to corticosteroids.

BRIEF SUMMARY OF THE INVENTION

In order to solve this problem, the present invention proposes using collagen hydrolysate as an active substance in the treatment of inflammatory skin disorders and intestinal disorders and/or skin disorders and intestinal disorders accompanied by inflammation. An appropriate efficacy of collagen hydrolysate has become evident in particular from a clinical study in which collagen hydrolysate or a placebo was administered to patients with neurodermatitis.

DETAILED DESCRIPTION OF THE INVENTION

Figure 1:
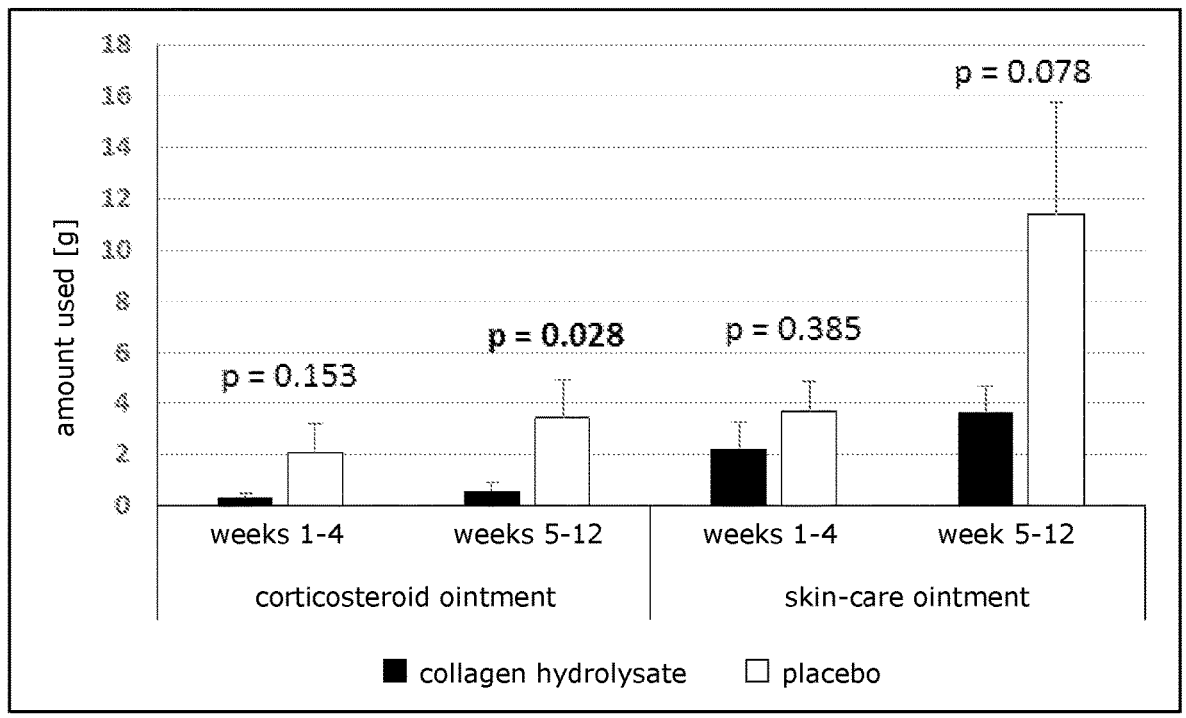
FIG. 1 shows a bar chart regarding the use of corticosteroid and skin-care ointment during the study period.

Various advantageous effects of collagen hydrolysate have already been known for a relatively long time, in particular the use of collagen hydrolysate in osteoporosis or in joint complaints. Positive effects of collagen hydrolysate on the health of the skin have also been described already, for example in international patent application WO 2012/065782 A2. Nevertheless, the efficacy of collagen hydrolysate in the treatment of neurodermatitis and other inflammatory disorders is surprising.

Collagen hydrolysate, as a by-product of animal starting materials which are also used as foodstuffs, is a completely harmless product from a health point of view with no known harmful side effects. It does not require legal approval as a drug, and can be marketed and used in particular in the form of a dietary supplement. Use of collagen hydrolysate as a dietary supplement, as a prescription-free (OTC) drug or as a prescription drug (in particular in combination with other active substances) is included within the scope of the present invention.

Collagen hydrolysate ideally is administered orally. It is known that the peptides of collagen hydrolysate are resorbed in the intestine at least to a certain extent even with relatively high molecular weights of up to 10,000 Da. The preferred amount of orally administered collagen hydrolysate in the case of a daily dose is from 2 to 15 g, more preferably from 3 to 10 g. A positive effect in the case of neurodermatitis could be demonstrated for example with a daily dose of 5 g collagen hydrolysate.

In a preferred embodiment of the invention the collagen hydrolysate is used as supportive treatment in addition to a treatment of the skin or intestinal disorder with a corticosteroid. Although it is not often possible to dispense entirely with a corticosteroid and still sufficiently ease the symptoms, the administration of collagen hydrolysate does make it possible to at least reduce the administered amount of corticosteroid, which in itself already results in a significant improvement of the side effects for the affected individuals.

The corticosteroid alongside which the collagen hydrolysate can be used in accordance with the invention is generally administered topically, in particular in the form of an ointment. Alternatively, oral administration of corticosteroids is also possible. In this latter case, in accordance with a further embodiment of the invention, a composition can be administered which contains the collagen hydrolysate and the corticosteroid, i.e. in the form of a combination preparation.

The corticosteroid is preferably a glucocorticoid, for example hydrocortisone. A large number of glucocorticoids are known which are divided into four classes from "hardly effective" (class I) to "very highly effective" (class IV).

A preferred embodiment of the invention relates to collagen hydrolysate for use as an active substance in the treatment of neurodermatitis. Further inflammatory skin disorders and/or skin disorders accompanied by inflammation, the treatment or supportive treatment of which with collagen hydrolysate is possible, are psoriasis, rosacea, chronic pruritus, acne, cellulitis and dermatoporosis.

The invention also comprises collagen hydrolysate for use in the treatment of inflammatory intestinal disorders and/or intestinal disorders accompanied by inflammation. Similarities exist between inflammatory disorders of the skin and intestine insofar as the intestinal wall contains collagen fibres as structural proteins and represents a barrier between the actual inside of the body and the "outer region". Intestinal disorders for the treatment of which it is possible to use collagen hydrolysate within the scope of the invention are, in particular, Crohn's disease and ulcerative colitis. These are each chronic inflammatory intestinal disorders which can be treated symptomatically with glucocorticoids.

A further aspect of the invention relates to collagen hydrolysate for use as an active substance to alleviate side effects of corticosteroids, in particular their side effects on the skin, such as skin atrophy, pigment disorders and ecchymosis. Corresponding information can also be found in the clinical study already mentioned, which will be discussed in detail further below.

The above-mentioned side effects of corticosteroids (in particular of glucocorticoids) are caused at least in part by a reduction of the collagen biosynthesis by the skin cells (fibroblasts) (see for example Oikarinen et al., Journal of Investigative Dermatology 98 (1992) 220-225). Cell tests in vitro have surprisingly found (see below) that this reduction of collagen biosynthesis can be almost fully compensated by the presence of collagen hydrolysate.

The collagen hydrolysate for use according to the invention typically has a mean molecular weight of from 500 to 15,000 Da, preferably from 1,000 to 8,000 Da, more preferably from 1,500 to 5,000 Da, most preferably from 1,800 to 2,200 Da. In these statements the weight-average molecular weight is always meant, which can be determined in particular by gel permeation chromatography.

The collagen hydrolysate is preferably produced by enzymatic hydrolysis of a collagen-containing starting material. In particular, endopeptidases or exopeptidases of microbial or plant origin are used for this hydrolysis. Collagen hydrolysates in the desired molecular weight range can be produced by suitable selection of the peptidases and the hydrolysis conditions.

The collagen-containing starting material is generally selected from skin or bone of vertebrates, preferably of mammals or birds, and in particular from the skin of cattle or pigs (bovine split hide or pork rind respectively). Alternatively, the collagen-containing starting material can be selected from skin, bone and/or scales of fish, in particular cold-water fish or tropical fish.

The collagen hydrolysate can be produced either in a one-stage method from these starting materials or by means of the intermediate stage gelatine; in the latter case, gelatine both of type A and of type B can be used.

The collagen hydrolysate is preferably produced by the successive action of at least two endoproteases having a different specificity, in particular of at least two different metalloproteases and/or serine proteases, i.e. of proteases that cleave the amino acid sequence of the collagen molecules before or after specific amino acids. The metalloproteases and/or serine proteases are expediently enzymes from the microorganisms *Bacillus subtilis, Bacillus licheniformis, Bacillus amyloliquefaciens, Aspergillus oryzae* and *Aspergillus melleus*.

Due to the selection of suitable endoproteases, not only can a specific molecular weight distribution of the collagen hydrolysate be obtained, but the type of amino acids at the termini of the peptides contained in the hydrolysate is also influenced. In this respect it is preferred, for example, if at least 50% of the N-terminal amino acids of the collagen hydrolysate are hydrophobic amino acids, in particular alanine, leucine and isoleucine.

Alternatively to the enzymatic hydrolysis, the collagen hydrolysate can be produced by recombinant gene expression within the scope of the invention. By use of natural collagen sequences, in particular from cattle or pigs, and expression thereof in genetically modified cells (for example yeasts, bacteria or plant cells, in particular tobacco), products can be produced that are substantially identical to the hydrolysis products of the corresponding collagen-containing raw materials. It is possible here to obtain a narrower or precisely specified molecular weight distribution.

The efficacy of collagen hydrolysate in the treatment of neurodermatitis will be explained in greater detail on the basis of the clinical study described hereinafter.

Furthermore, cell tests in vitro which demonstrate the efficacy of collagen hydrolysate in the alleviation of the side effects of corticosteroids are described.

The following examples further illustrate the invention but, of course, should not be construed as in any way limiting its scope.

EXAMPLE 1

Clinical Study
Study Design

The clinical study was performed with thirty test subjects (15 men and 15 women) diagnosed with neurodermatitis, with the degree of severity of the neurodermatitis being in the range of from 15 to 40 in all test subjects according to the SCORAD index. The study was a randomised, double-blind, placebo-controlled study, i.e. the test subjects were divided randomly into a treatment group and a placebo group containing 15 individuals each, with neither the test subjects nor the treating staff being aware of the group allocation of the individual test subjects.

The test subjects in the treatment group received a daily dose of 5 g collagen hydrolysate during the entire study period of 12 weeks. This was the product Verisol B, distributed by the applicant, which is a collagen hydrolysate produced by enzymatic hydrolysis of bovine collagen with a mean molecular weight of approximately 2,000 Da. The production method for Verisol B corresponds substantially to the production method described in WO 2012/065782 A2.

The test subjects in the placebo group received a daily dose of 5 g maltodextrin instead of the collagen hydrolysate; the collagen hydrolysate and the placebo did not differ in respect of packaging, texture or taste.

During the study, the test subjects were free to choose whether, and in what amount, to apply a skin-care ointment (unguentum leniens) or a corticosteroid-containing ointment (triamcinolone acetonide) to ease the symptoms. The used amounts of skin-care ointment and corticosteroid for each individual test subject were measured during the study period.

Use of Skin-Care Ointment and Corticosteroid

A noticeable result of the study is that the use both of skin-care ointment and of corticosteroid-containing ointment in the investigation group is significantly lower than in the placebo group. This is true both for the first third (4 weeks) of the study period and for the period from the 5th week to the 12th week, and in each case is particularly pronounced for the use of corticosteroid.

FIG. 1 shows the corresponding results in the form of a bar chart, i.e. the average use of corticosteroid-containing ointment and skin-care ointment in grams in both groups for the respective time periods.

This result demonstrates the efficacy of collagen hydrolysate in the treatment of neurodermatitis. Since the amount of corticosteroid and skin-care ointment could be selected freely by the test subjects as required, the smaller required amount in the investigation group can only be explained by the fact that some of the symptoms were able to be eased directly by the orally administered collagen hydrolysate.

Measurement of the pH Value of the Skin

The pH value of the skin, which is an indicator for its barrier function, was measured in all test subjects at the start of the study, after four weeks and after twelve weeks using a skin pH meter (Courage+Khazaka electronic GmbH). The measurements were performed in the region of the upper arm, more specifically both in healthy skin areas and in skin areas affected by lesions.

Figure 2:
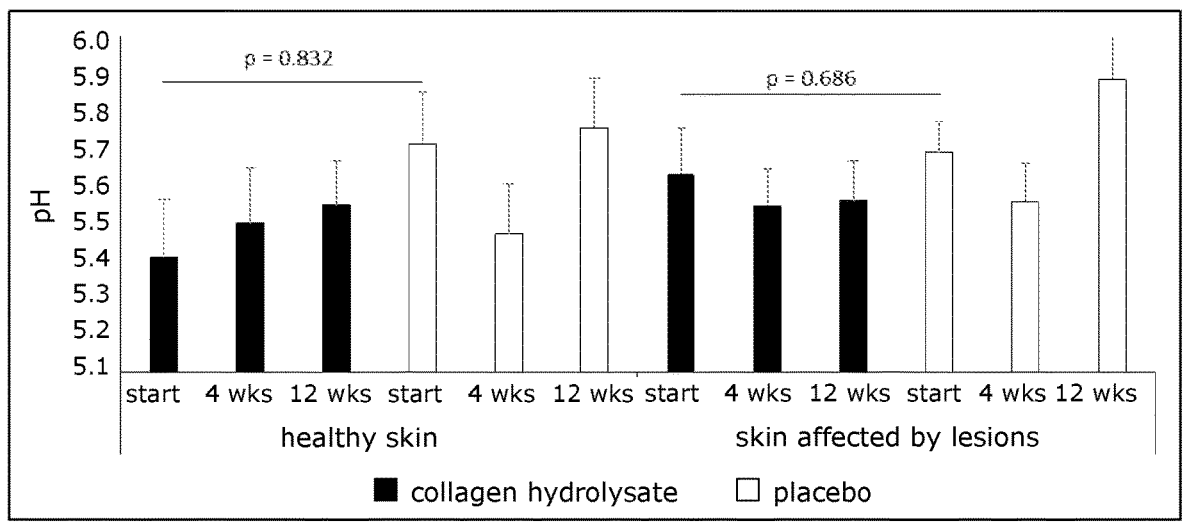
FIG. 2 shows a bar chart regarding the development of the pH value of the skin during the study period.

The results are shown in FIG. 2 in the form of a bar chart.

In the treatment group the pH value of skin areas with lesions tended to approach the pH value of healthy skin in the range of from 5.3 to 5.6 during the course of the study period. By contrast, in the placebo group the pH value both of healthy skin and of skin areas with lesions increased abnormally after twelve weeks.

This result leads to the conclusion that oral administration of collagen hydrolysate at least partially counteracts the side effects of corticosteroids on the skin.

Transepidermal Water Loss and Skin Moisture

Measurements of the transepidermal water loss (TEWL) using a Tewameter and of skin moisture using a Corneometer (both from Courage+Khazaka electronic GmbH) were also taken during the study period. Both parameters, similarly to pH value, are indicators for skin barrier function.

No significant differences between the treatment group and the placebo group were found in the results for these two parameters, neither in healthy skin areas nor in skin areas affected by lesions. This leads indirectly to the conclusion that, in spite of the higher amount of used corticosteroid in the placebo group and its side effects, no deterioration of the parameters occurred there, which might be attributable to the effect of the collagen hydrolysate.

Assessment of Itching

An assessment of itching was performed on the test subjects during the study period in accordance with a model called the "5-D Pruritus Scale". According to this model, itching is assessed both quantitatively and qualitatively (duration, severity and tendency), in respect of localisation on the body (distribution), and also in respect of impairment of the following areas of life as a result of the itching: sleep; free time/social activities; housework/errands; work/school.

Figure 3:
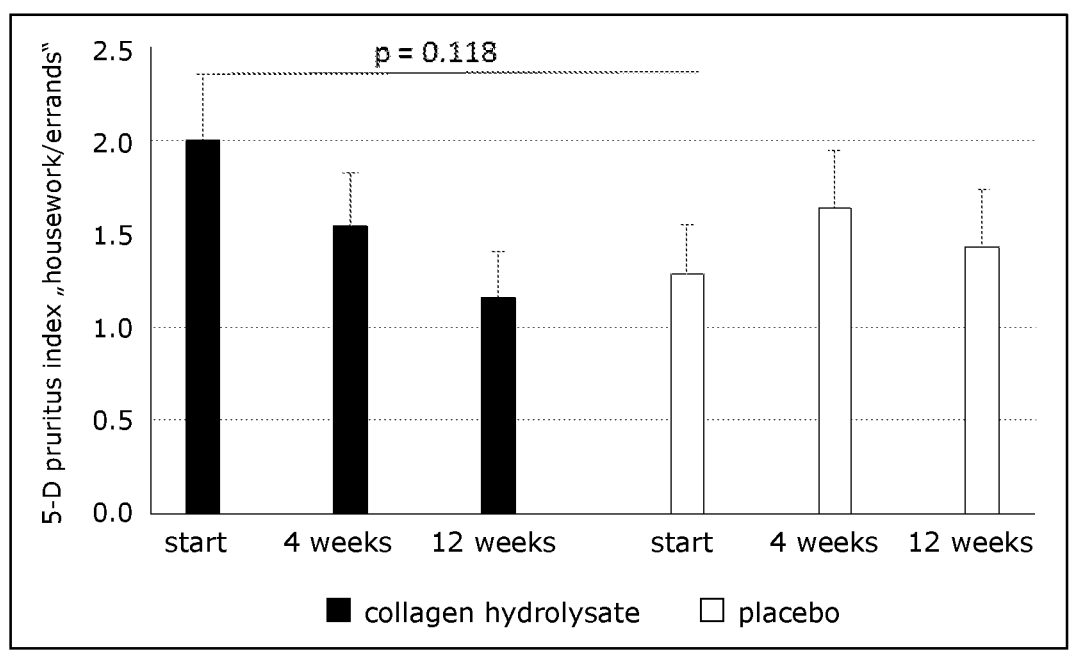
FIG. 3 shows a bar chart regarding the change to the index "impairment of housework/errands due to itching" during the study period.

For the assessment criterion "impairment of housework/errands", a significant improvement in the index was seen in the treatment group during the study period in contrast to the placebo group. The corresponding results are shown in the bar chart in FIG. 3 (mean values of the index at the start of the study, after four weeks and after twelve weeks). This result is a direct reflection of efficacy of the collagen hydrolysate in the alleviation of itching.

For the other assessment criteria there were no significant differences in the various indices between the investigation group and the placebo group. Under consideration of the fact that much more corticosteroid was used in the placebo group, however, this finding also indirectly leads to the conclusion that the effect of the corticosteroid could be replaced at least in part by collagen hydrolysate.

EXAMPLE 2

Cell Tests In Vitro
Cell Tests with Fibroblasts

A topical treatment with corticosteroids is associated in particular with longer treatment period with negative side effects, such as skin atrophy. A key cause of these side effects is the reduction of the biosynthesis of collagen, and also of other key matrix proteins such as proteoglycans, by the fibroblasts.

Cell tests with human fibroblasts were performed to investigate whether collagen hydrolysate in combination with glucocorticoids has an influence on the biosynthesis of the matrix proteins. The same collagen hydrolysate (Verisol B) was used for these tests as in the above-described clinical study.

Primary human fibroblasts were cultivated in HAM's F12 medium, which was supplemented with 10% foetal bovine serum, 20 U/ml penicillin streptomycin, 50 µg/ml patricin, 0.05 mg/ml ascorbic acid and 0.15 mg/ml glutamine. After reaching a confluence of the cells of 80%, the culture medium was replaced in three different batches with fresh medium which was supplemented with 0.5 mg/ml collagen hydrolysate, with 0.05 mg/ml of a glucocorticoid (dexamethasone) or with a combination of both components. A control batch was cultivated further in the culture medium without additions.

After a further cultivation of seven days, the amount of the extracellular matrix proteins synthesised by the fibroblasts was determined, with collagen type I being determined by the "Sircol Soluble Collagen Assay" and proteoglycans being determined by the "Glycosaminoglycan Assay Blyscan" (Biocolor Ltd, Great Britain), in each case in accordance with the manufacturer's instructions.

Figure 4:
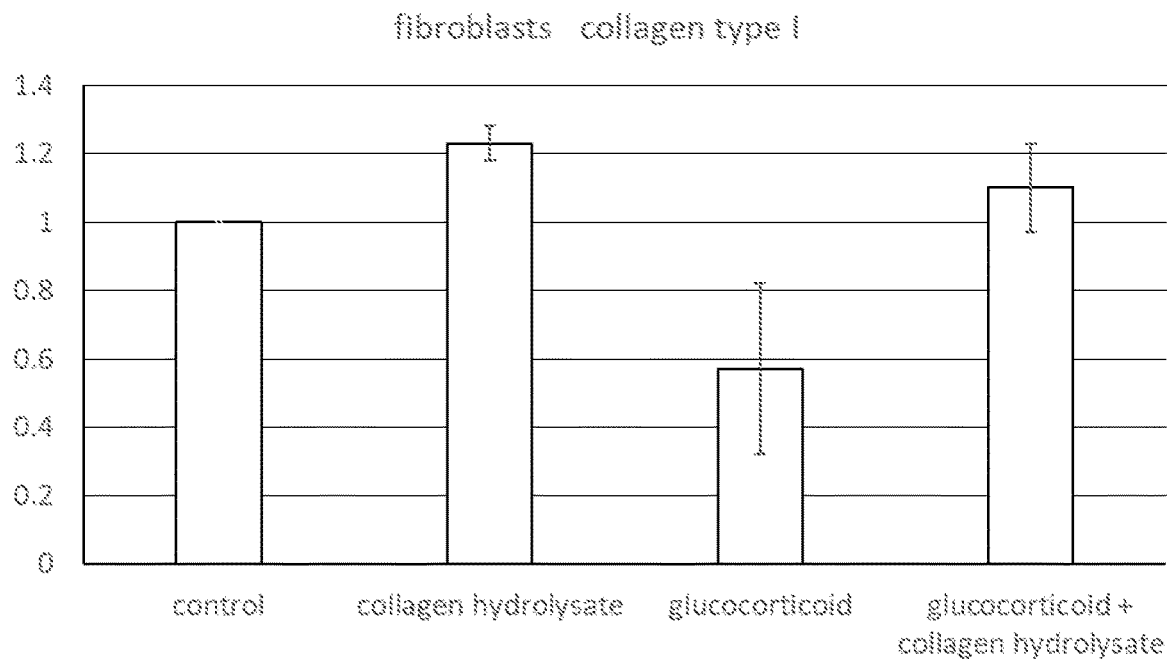
FIGS. 4A-4B show bar charts regarding the biosynthesis of collagen type I (A) and proteoglycans (B) by fibroblasts.
Figure 4:
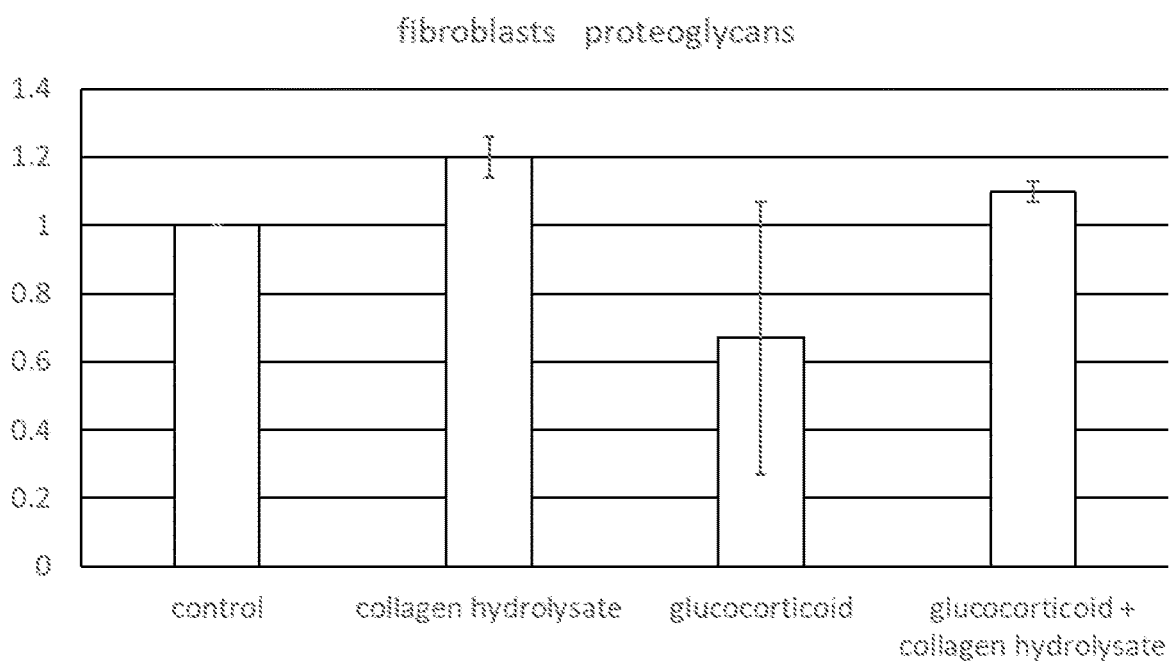

The results are shown in the bar charts in FIGS. 4A-4B, in which FIG. 4A relates to the biosynthesis of collagen type I and FIG. 4B relates to the biosynthesis of proteoglycans. In each case mean values from eight tests are specified in relation to the control batch. In both cases it can firstly be seen that the biosynthesis of collagen and proteoglycan is significantly reduced by glucocorticoids, as expected. This reduction can be fully compensated, however, by additional supplementation with collagen hydrolysate. Collagen hydrolysate on its own has a mildly stimulating effect on the biosynthesis.

These results are a further indication that the side effects of corticosteroids, such as skin atrophy, which are caused by a reduction of the biosynthesis of matrix proteins in skin cells, can be reduced by the administration of collagen hydrolysate.

Cell Tests with Chondrocytes

The same cell tests were also performed with human chondrocytes (cartilage cells). The cultivation of the cells and determination of collagen type I and biproteoglycans were performed as in the above-described tests with fibroblasts, with the difference that a collagen hydrolysate from bovine bone gelatine with a mean molecular weight of approximately 4,000 Da was used.

Figure 5:
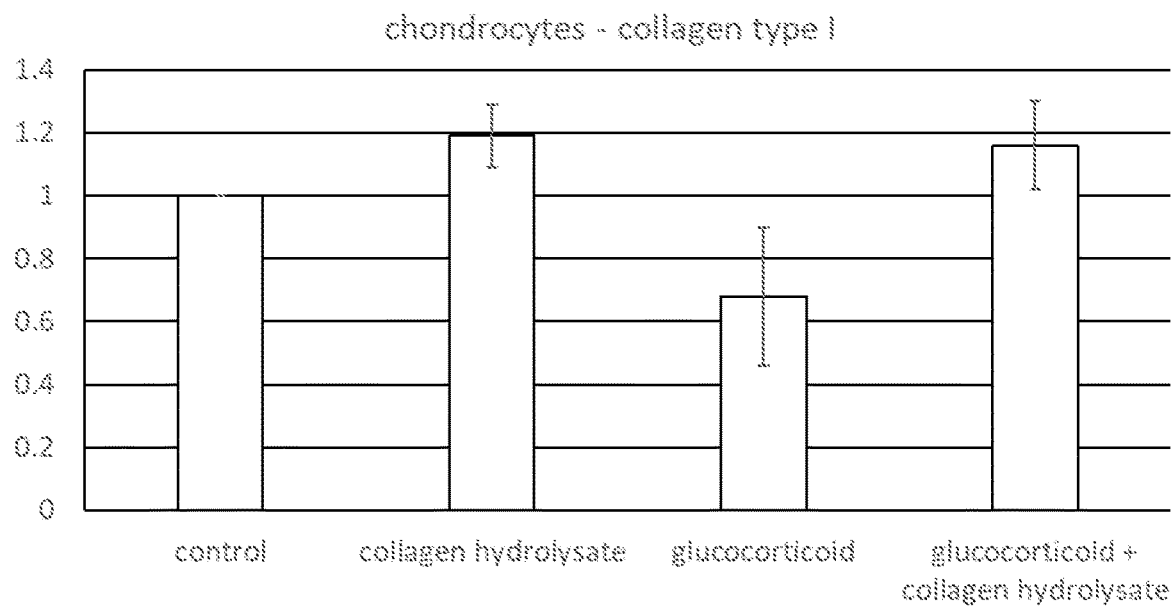
FIGS. 5A-5B show bar charts regarding the biosynthesis of collagen type I (A) and proteoglycans (B) by chondrocytes.
Figure 5:
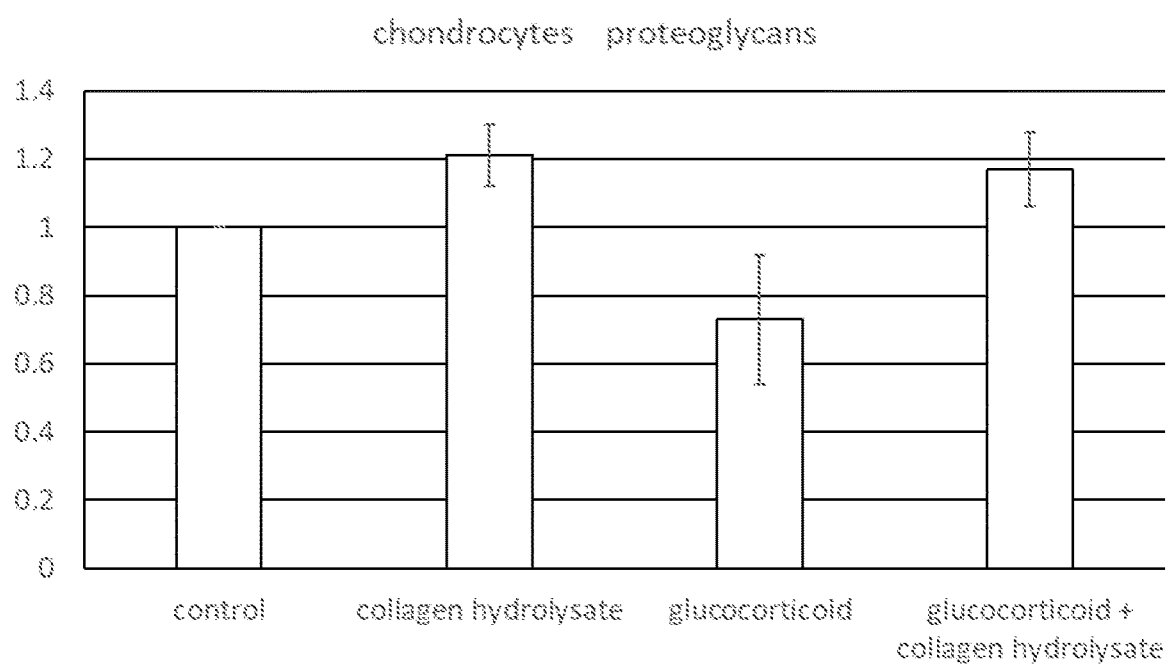

The results are shown in the bar charts of FIGS. 5A-5B, in which FIG. 5A shows the biosynthesis of collagen type I and FIG. 5B shows the biosynthesis of proteoglycans. In each case the mean values from three tests are shown. Here too, it can be seen that the reduction in biosynthesis caused by the glucocorticoid can be substantially fully compensated by the addition of collagen hydrolysate.

Cell Tests with Osteoblasts

Figure 6:
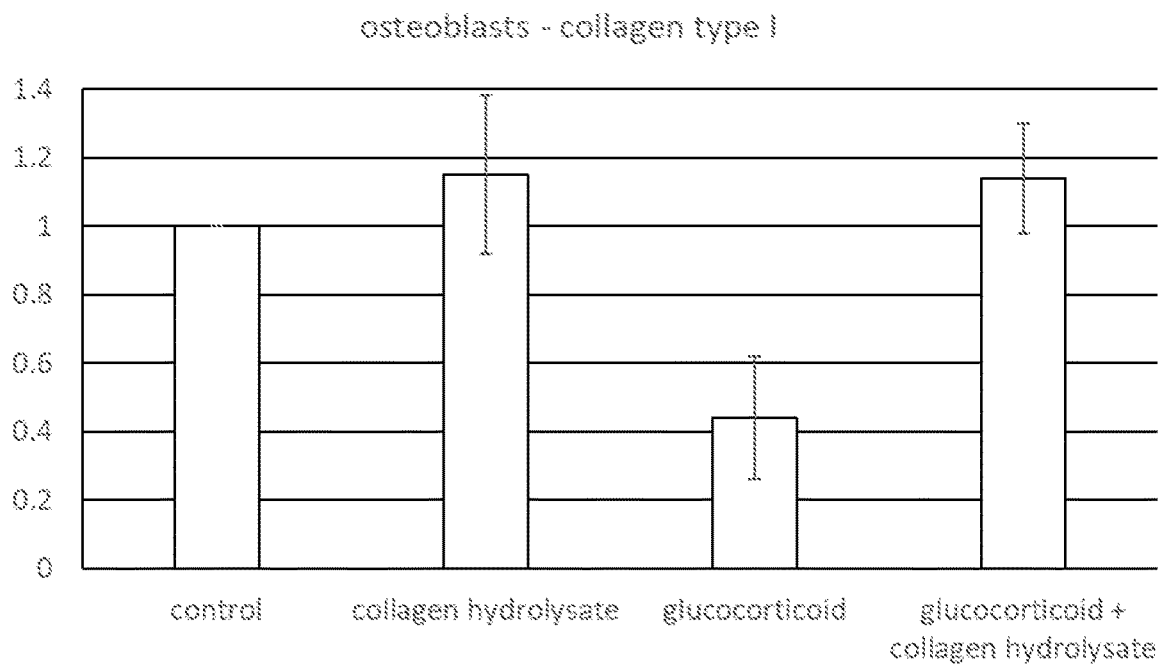
FIGS. 6A-6B show bar charts regarding the biosynthesis of collagen type I (A) and proteoglycans (B) by osteoblasts.
Figure 6:
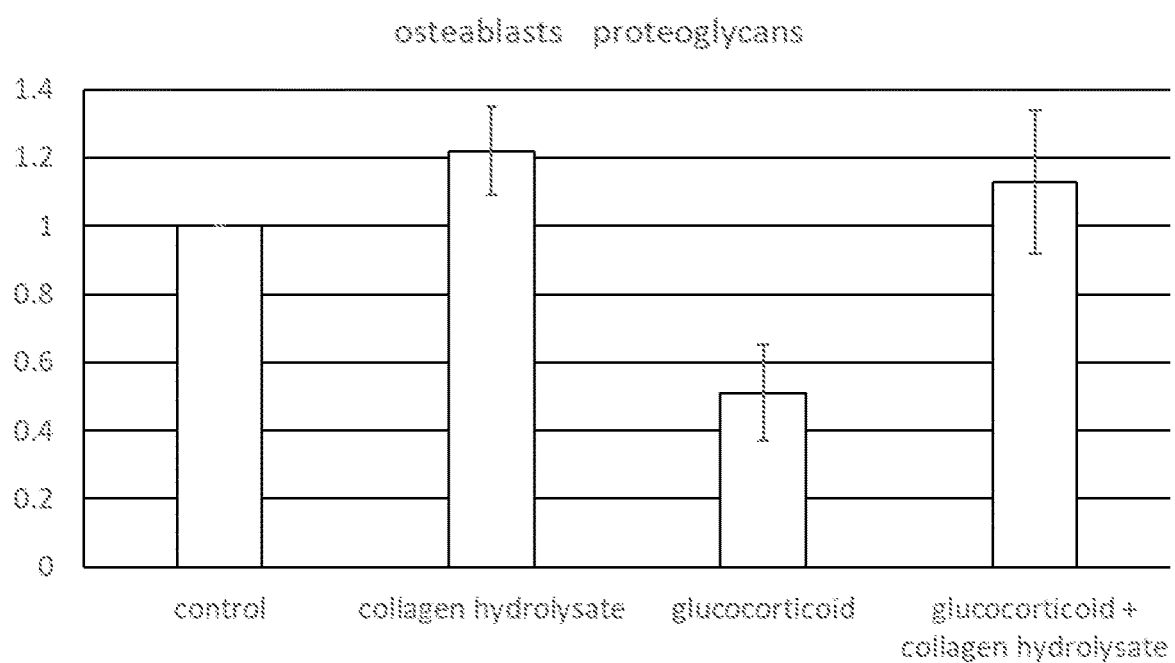

Corresponding tests were also performed with human osteoblasts (bone cells); the tests were performed and the collagen type I and proteoglycans determined in the same way as for the tests with chondrocytes (inclusive of the collagen hydrolysate with 4,000 Da). The bar charts in FIGS. 6A-6B show that, also in the case of osteoblasts, the reduction of the biosynthesis of collagen type I (FIG. 6A) and of proteoglycans (FIG. 6B) by the glucocorticoid can be substantially fully compensated by the addition of collagen hydrolysate.

The results with chondrocytes and osteoblasts show that the advantageous effects of collagen hydrolysate in combination with corticosteroids are not limited to the skin, and that an alleviation of side effects can also be expected in other tissue types.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating neurodermatitis in a patient in need thereof, the method comprising orally administering collagen hydrolysate to the patient.

2. The method according to claim 1, comprising using the collagen hydrolysate as a supportive treatment in addition to treating the neurodermatitis by administering a corticosteroid to the patient.

3. The method according to claim 2, wherein administering the collagen hydrolysate allows a reduction of the administered amount of corticosteroid.

4. The method according to claim 2, comprising administering the corticosteroid topically.

5. The method according to claim 2, comprising administering the corticosteroid orally.

6. The method according to claim 2, wherein the corticosteroid is a glucocorticoid.

7. The method according to claim 1, wherein the collagen hydrolysate has a mean molecular weight of from 500 to 15,000 Da.

8. The method according to claim 1, wherein the collagen hydrolysate is produced by enzymatic hydrolysis of a collagen-containing starting material.

9. The method according to claim 8, wherein the collagen-containing starting material is selected from skin or bone of vertebrates.

10. The method according to claim 8, wherein the collagen hydrolysate is produced by successive action of at least two endoproteases having a different specificity.

11. The method according to claim 10, wherein the endoproteases are selected from enzymes from microorganisms *Bacillus subtilis, Bacillus licheniformis, Bacillus amyloliquefaciens, Aspergillus oryzae* and *Aspergillus melleus*.

12. The method according to claim 1, wherein at least 50% of the N-terminal amino acids of the collagen hydrolysate are hydrophobic amino acids.

13. The method according to claim 1, wherein the collagen hydrolysate is produced by recombinant gene expression.

14. The method according to claim 1, comprising administering the collagen hydrolysate in a daily dose of from 2 to 15 g.

15. The method according to claim 5, comprising administering a composition which contains the collagen hydrolysate and the corticosteroid to the patient.

\* \* \* \* \*